US007751602B2

(12) United States Patent
Collins et al.

(10) Patent No.: US 7,751,602 B2
(45) Date of Patent: Jul. 6, 2010

(54) SYSTEMS AND METHODS OF CLASSIFICATION UTILIZING INTENSITY AND SPATIAL DATA

(75) Inventors: Louis Collins, St-Lambert (CA); Simon Duchesne, Montreal (CA)

(73) Assignee: McGill University, Montreal, Quebec (CA)

( * ) Notice: Subject to any disclaimer, the term of this patent is extended or adjusted under 35 U.S.C. 154(b) by 1105 days.

(21) Appl. No.: 10/990,396

(22) Filed: Nov. 18, 2004

(65) Prior Publication Data

US 2006/0104494 A1 May 18, 2006

(51) Int. Cl.
*G06K 9/00* (2006.01)

(52) U.S. Cl. .................. 382/128; 382/159; 382/228

(58) Field of Classification Search ............... None
See application file for complete search history.

(56) References Cited

U.S. PATENT DOCUMENTS

2004/0175034 A1    9/2004  Wiemker et al.

OTHER PUBLICATIONS

S. Duchesne, N. Bernasconi, A. Bernasconi and D.L. Collins; On the classification of temporal lobe epilepsy using MR image appearance 2002; IEEE computer society, 1: 520-523.*
A Short History of Statistical Parametric Mapping in Functional Neuroimaging Prepared as background for an article by Peter Bandettini "The Inception of SPM and Modern-day Brain Mapping"pp. 1-8 The URL of this document is: http://www.fil.ion.bpmf. ac.uk/spm/history.html downloaded on Oct. 24, 2004.

"Automatic 3D Intersubject Registration of MR Volumetric Data in Standardized Talairach Space" D. Louis Collins, Peter Neelin, Terrence M. Peters, and Alan C. Evans, Journal of Computer Assisted Tomography 18(2):192-205, Mar./Apr. 1994 Raven Press, Ltd., New York.
"Automatic 3D Model-Based Neuroanatomical Segmentation" D.L. Collins, C.J. Holmes, T.M. Peters, and A.C. Evans, McConnell Brain Imaging Centre, Montreal Neurological Institute, McGill Univesity, Montreal, Canada, Human Brain Mapping 3:190-208(1995).
"A Nonparametric Method for Automatic Correction of Intensity Nonuniformity in MRI Data" John G. Sled, Alex P. Zijdenbos, Member IEEE, and Alan C. Evans, IEEE Transactions On Medical Imaging, vol. 17, No. 1, Feb. 1998 pp. 87-97.

(Continued)

*Primary Examiner*—Vu Le
*Assistant Examiner*—Claire Wang
(74) *Attorney, Agent, or Firm*—Anglehart et al.

(57) ABSTRACT

A method of classifying a test subject comprises collecting imaging data for a plurality of training subjects, control subjects and a test subject. An intensity volume of interest (VOI) and a morphological VOI are selected from said imaging data. Training intensity data and morphological data are calculated for the intensity and spatial VOI. A statistical model can then be created based on the training intensity data and training spatial data to provide a universe of subjects. Control intensity data and spatial data are also calculated for the intensity and spatial VOI. A classifier can then be built dividing the universe into at least two regions. The test subject data can then be applied to the classifier to provide a determination of whether the test subject falls within the first region or the second region. The condition can be a neurological disease state such as temporal lobe epilepsy or Alzheimer's dementia.

23 Claims, 9 Drawing Sheets

OTHER PUBLICATIONS

"Differences in frontal cortical activation by a working memory task after substitution of risperidone for typical antipsychotic drugs in patients with schizophrenia" Garry D. Honey, Edward T. Bullmore, William Soni, Malini Varatheesan, Steve C.R. Williams, and Tonmoy Sharma, PNAS, vol. 96, Issue 23, 13432-13437, Nov. 9, 1999 pp. 1-16 The URL of this document is: http://www.pnas.org/cgi/content/full/96/23/13432.

"A Unified Statistical Approach to Deformation-Based Morphometry" M.K. Chung, K.J. Worsley, T. Paus, C. Cherif, D.L. Collins, J.N. Giedd, J.L. Rapoport, and A.C. Evans, NeuroImage doi:10.1006/nimg.2001.0862, available online at http://www.idealibrary.com on IDEAL, Received Aug. 14, 2001 pp. 1-11.

"Physiological Dysfunction of the Dorsolateral Prefrontal Cortext in Schizophrenia Revisited" Joseph H. Callicott, Alessandro Bertolino, Venkata S. Mattay, Frederick J.P. Langheim, Jeffrey Duyn, Richard Coppola, Terry E. Goldberg and Daniel R. Weinberger, Cerebral Cortex, vol. 10, No. 11, 1078-1092, Nov. 2000 pp. 1-32 The URL of this document is http://cercor.oupjournals.org/cgi/content/full/10/11/1078.

"Statistical models of appearance for medical image analysis and computer vision" T.F. Cootes and C.J. Taylor, Imaging Science and Biomedical Engineering, University of Manchester, UK, This paper appears in Proc. SPIE Medical Imaging, 2001.

"4D Deformation Modeling of Cortical Disease Progression in Alzheimer's Dementia" Andrew L. Janke, Greig de Zubicaray, Stephen E. Rose, Mark Griffin, Jonathan B. Chalk, and Graham J. Calloway, Magnetic Resonance in Medecine 46:661-666 (2001).

"Active Appearance Models" Timothy F. Cootes, Gareth J. Edwars, and Christopher J. Taylor, IEEE Transactions on Pattern Analysis and Machine Intelligence, vol. 23, No. 6, Jun. 2001 pp. 681-685.

"Appearance-Based Segmentation of Medial Temporal Lobe Structures" S. Duchesne, J.C. Pruessner, and D.L. Collins, McConnell Brian Imaging Centre, Montreal Neurological Institute, McGill University, 3801 University Street, Montreal, Canada H3A 2B4, NeuroImage 17, 515-531 (2002) doi:10.1006/nimg.2002.1188.

"Survey of brain imaging techniques with implications for nanomedicine" Stephen S. Flitman, MD, Cognitive Neurology Section, Barrow Neurological Institute, Phoenix, Arizona, USA, Foresight Institute, Last updated Jul. 17, 2002 pp. 1-9 The URL of this document is: http://www.foresight.org.Conferences/MNT8/Papers/Flitman/index.html.

"On the classification of temporal lobe epilepsy using MR image appearance" S. Duchesne, N. Bernasconi, A. Bernasconi and D.L. Collins, Proc. 16th International Conference on Pattern Recognition, R. Katsuri, D. Laurendeau and C. Suen, editors, IEEE Computer Society, 1:520-523; 2002.

"Mapping the evolution of regional atrophy in Alzheimer's disease: Unbiased analysis of fluid-registered serial MRI" Rachael I. Scahill, Jonathan M. Schott, John M. Stevens, Martin N. Rossor, and Nick C. Fox, PNAS, Apr. 2, 2002, vol. 99, No. 7, 4703-4707, pp. 1-15 The URL of this page is: http://www.pnas.org/cgi/content/full/99/7/4703.

"Statistical Parametric Mapping SPM2" Developed by members & collaborators of the Wellcome Department of Imaging Neuroscience, SPM2—release May 12, 2003 The URL of this document is: http://www.fil.ion.bpmf.ac.uk/spm/spm2/html pp. 1-14 and pp. 1 & 2.

"Temporal lobe epilepsy lateralization based on MR image intensity and registration features" S. Duchesne, N. Bernasconi, A. Janke, A. Bernasconi, and D.L. Collins, Proceedings of Medical Image Processing and Computer-Assisted Intervention, Ellis RE, Peters TM (Eds), 2879(1): 367-374, Nov. 19, 2003.

"Within-group nonlinear registration improves between-group Voxel-Based Morphometry" S. Duchesne, N. Bernasconi, A. Janke, K. Worsley, A. Bernasconi and D.L Collins, Proc. International Society for magnetic Resonance in Medicine, ISMRM, Toronto, Canada, Jul. 2003, published Dec. 22, 2003 pp. 1-22.

"Efficient Principal Component Analysis for Multivariate 3D Voxel-Based Mapping of Brain Functionnal Imaging Data Sets as Applied to FDG-PET and Normal Aging" Gerhard Zuendorf, Nacer Kerrouche, Karl Herzholz, and Jean-Claude Baron, Human Brain Mapping 18:13-21 (2003).

"Linear Discriminant Analysis—A Brief Tutorial" S. Balakrishnama, A. Ganapathiraju, downloaded from lcv.stat.fsu.edu/research/geometrical-representations-of-faces/PAPERS/lda-theory.pdf (around Oct. 24, 2004).

"Principal components analysis" Encyclopedia article about Principal components analysis, TheFreeDictionary.com, 2004 Farlex, Inc. The URL of this document is: http://encyclopedia.thefreedictionary.com/Principal%20components%20analysis pp. 1-5, downloaded on Oct. 20, 2004.

* cited by examiner

SYSTEMS AND METHODS OF CLASSIFICATION UTILIZING INTENSITY AND SPATIAL DATA

FIELD OF THE INVENTION

The present invention relates generally to systems and methods of classification utilizing imaging data. This invention has particular, but not exclusive application as a computer-aided method and system of achieving diagnosis of neurological diseases or disorders in subjects, via analysis of in vivo medical images of the brain.

BACKGROUND OF THE INVENTION

The quantitative analysis of in vivo medical images of the human brain is a growing field of activity and research. A general approach for diagnosis is to detect subtle differences in the composition, morphology or other behavior in the brain as can be imaged by different techniques and equipment (ie. modalities) and relate these differences to clinical phenomena of interest.

Image data can be obtained from various sources including T1 weighted Magnetic Resonance Imaging ("T1w MRI"), T2 weighted MRI ("T2w MRI"), Proton Density weighted MRI ("PD MRI"), Photon Emission Tomography ("PET"), Single Photon Emission Computer Tomography ("SPECT") and Computer Tomography ("CT").

Classification of neurological diseases based solely on their imaging characteristics is a challenging task for computer vision. If successful, however, classification systems based on image data of the brain, can serve multiple purposes such as computer-assisted diagnosis, disease characterization or the morphological assessment of drug effect.

Most of the work to date on automated or semi-automated classification of various neurological diseases performed using MRI images of the human brain, such as T1w MRI, has focused on individual brain structures that have either clear boundaries, or form a cohesive entity that can be segmented easily. Examples of the former include the ventricles and corpus callosum, while one of the most notable cases of the latter is the hippocampus (HC), a medial temporal lobe (MTL) structure that plays a central role in many pathological processes.

Volumetry in the context of the study of the brain, relates generally to taking various measurements of the volume of a structure within of the brain, and reaching conclusions based on such measurements. Based on manual or automated segmentation, it is the primary indicator of structure integrity. Volumetry results in epilepsy have been published in Jack C R, Jr., "MRI-based hippocampal volume measurements in epilepsy", Epilepsia 1994, 35 Suppl 6: S21-9; Watson C, Cendes F, Fuerst D, Dubeau F, Williamson B, Evans A, Andermann F, "Specificity of volumetric magnetic resonance imaging in detecting hippocampal sclerosis", Arch Neurol 1997, 54(1):67-73; and Bernasconi N, Bernasconi A, Caramanos Z, Antel S B, Andermann F, Arnold D L, "Mesial temporal damage in temporal lobe epilepsy: a volumetric MRI study of the hippocampus, amygdala and parahippocampal region", Brain 2003; 126(Pt 2):462-9, the contents of each being incorporated herein by reference. Chetelat G, Baron J C, "Early diagnosis of Alzheimer's disease: contribution of structural neuroimaging", Neuroimage 2003, 18(2): 525-41, proposes a review of the subject as relating to Alzheimer's dementia, the contents of which are incorporated herein by reference. Obtaining manual volumetric results is resource intensive and necessitates neuroanatomical expertise.

In looking at a volume of the brain, the T1w MRI intensity can be used as an indicator of the progression of a disease, where subtle changes in the signal may indicate an underlying pathological process before structure integrity is lost. Some methods have used the intensity signal directly, such as Webb et al. in an application on temporal lobe epilepsy described in Webb J, Guimond A, Eldridge P, Chadwick D, Meunier J, Thirion J P, Roberts N, "Automatic detection of hippocampal atrophy on magnetic resonance images", Magn Reson Imaging 1999, 17(8): 1149-61, the contents of which are incorporated herein by reference. Others have employed higher order statistics for texture (voxel by voxel) analysis to identify cortical abnormalities in epilepsy and lateralize the seizure focus, as in Antel S B, Collins D L, Bernasconi N, Andermann F, Shinghal R, Kearney R E, Arnold D L, Bernasconi A, "Automated detection of focal cortical dysplasia lesions using computational models of their MRI characteristics and texture analysis", Neuroimage 2003, 19(4):1748-59, the contents of which are incorporated herein by reference.

Registration is a process also used in studying images of the brain. Individual subject images are aligned into a reference space, allowing spatial comparisons to be made between cohorts at the voxel level, such as in voxel-based morphometry or VBM as in Ashburner J, Friston K J, "Voxel-based morphometry—the methods", Neuroimage 2000, 11(6 Pt 1):805-21, the contents of which are incorporated herein by reference. Examples of VBM analysis in epilepsy research include Woermann F G, Free S L, Koepp M J, Ashburner J, Duncan J S, "Voxel-by-voxel comparison of automatically segmented cerebral gray matter—A rater-independent comparison of structural MRI in patients with epilepsy", Neuroimage 1999, 10(4):373-84; Keller S S, Wieshmann U C, Mackay C E, Denby C E, Webb J, Roberts N, "Voxel based morphometry of grey matter abnormalities in patients with medically intractable temporal lobe epilepsy: effects of side of seizure onset and epilepsy duration", J Neurol Neurosurg Psychiatry 2002, 73(6):648-55 and Bernasconi N, Duchesne S, Janke A, Lerch J, Collins D L, Bernasconi A, "Whole-brain voxel-based statistical analysis of gray matter and white matter in temporal lobe epilepsy", Neuroimage 2004, 23(2):717-23, the contents of each being incorporated herein by reference.

The registration process is typically broken down in a two-phase process to identify the linear and non-linear components required to align datasets. Linear transformation is used to correct global differences in brain size, orientation and shape. In a non-linear registration phase, a dense deformation field is estimated, which embeds unique spatial information about the individual brain under study. Morphometry based on the analysis of the deformation field is then possible, as proposed by Shen D, Moffat S, Resnick S M, Davatzikos C, "Measuring size and shape of the HC in MR images using a deformable shape model", Neuroimage 2002, 15(2):422-34 or Chung M K, Worsley K J, Robbins S, Paus T, Taylor J, Giedd J N, Rapoport J L, Evans A C, "Deformation-based surface morphometry applied to gray matter deformation", Neuroimage 2003, 18(2):198-213, the contents of each being incorporated herein by reference. This in turn enables surface analysis of individual structures to be conducted, such as analysis of the HC in Alzheimer's disease in Csernansky J G, Wang L, Joshi S, Miller J P, Gado M, Kido D, McKeel D, Morris J C, Miller M I, "Early Dementia of the Alzheimer type is distinguished from aging by high-dimensional mapping of the hippocampus", Neurology 2000, 55(11):1636-43 or schizophrenia in Csernansky J G, Schindler M K, Splinter N R, Wang L, Gado M, Selemon L D, Rastogi-Cruz D, Posener J A, Thompson P A, Miller M I, "Abnormalities of thalamic volume and shape in schizophrenia", Am J Psychiatry 2004, 161(5):896-902, the contents of each being incorporated herein by reference. Segmentation can be automated using a registration-based approach; once the structure has been identified, one can perform volumetric measurements as in Hogan R E, Bucholz R D, Choudhuri I, Mark K E, Butler C S, Joshi S, "Shape analysis of hippocampal surface structure in patients with unilateral mesial temporal sclerosis. J Digit Imaging 2000", 13(2 Suppl 1):39-42, or further analysis of intrinsic properties, such as medial sheets (which can be crudely thought of as the planar skeleton of an object) as described in Styner M, Gerig G, Lieberman J, Jones D, Weinberger D, "Statistical shape analysis of neuroanatomical structures based on medial models", Med Image Anal 2003, 7(3):207-20 and Joshi S, Pizer S, Fletcher P T, Yushkevich P, Thall A, Marron J S, "Multiscale deformable model segmentation and statistical shape analysis using medial descriptions", IEEE Trans Med Imaging 2002, 21(5):538-50, the contents of each being incorporated herein by reference.

The drawbacks of structure-centered analysis reside mostly in their reliance on manual or automated segmentation, a process with its own limitations. Moreover, interrelations between neighboring structures, critical in many pathologies, are not captured if only individual elements are measured.

It should also be noted that the analytical techniques referenced above use either intensity or registration information, one at the exclusion of the other.

SUMMARY OF THE INVENTION

A neurological disorder classification system based on brain images is disclosed which moves away from the structure-based paradigm. The invention (a) uses a relatively large, non-specific volume of interest (VOI) as opposed to focusing on a specific feature in the brain and (b) combines intensity and registration features for classification purposes.

It has been found that in at least some circumstances, the chosen VOI contains sufficient discriminatory information based on a combination of image intensity and registration features to effectively classify new subjects based on those features.

In one embodiment of the invention, a multidimensional eigenspace can be created by combining the results from Principal Component analyses of the following data: (a) linearly registered intensity images of a pre-selected volume of interest (VOI) and (b) an approximation of the determinant of the Jacobian matrix of the deformation field for the given VOI. The deformation fields can be obtained by non-linear registration of the VOI with a common reference image.

First, a multidimensional eigenspace or universe of subjects is created by using processed data from a large group of training subjects. Secondly, VOIs from a group of control subjects are projected into the multidimensional eigenspace. Linear discriminant analyses (LDA) is used to classify the control subjects, based on their expressed eigencoordinates in Principal Component (PC) space, and identify, from the distribution of coordinates, those principal components which hold the most diagnostic information. To classify a test subject, his/her VOIs are projected in the same space and the resulting coordinates are used to assess group membership.

According to one aspect of the invention there is provided a method of classifying a test subject. The method includes: collecting imaging data for a plurality of training subjects; collecting imaging data for a plurality of control subjects at least some of which are known to have a condition; collecting imaging data for the test subject; selecting an intensity volume of interest (VOI) for intensity analysis and a spatial volume of interest (VOI) for spatial analysis from the imaging data for the training subjects, the control subjects and the test subject; calculating training intensity data for the intensity VOI for the training subjects and calculating training spatial data for the spatial VOI for the training subjects; creating a statistical model based on the training intensity data and the training spatial data to provide a universe of subjects defined in relation to the intensity data and the spatial data; calculating control intensity data for the intensity VOI for the control subjects and calculating control spatial data for the control VOI for the control subjects; dividing the universe into at least a first region of subjects likely having the condition and a second region of subjects likely not having the condition utilizing the statistical model, control intensity data and the control spatial data; calculating subject intensity data for the intensity VOI for the test subject and calculating subject spatial data for the spatial VOI for the test subject; and applying the subject intensity data and the subject spatial data of the test subject to the classifier to provide a determination of whether the test subject falls within the first region or the second region.

According to another aspect of the invention there is provided a method of classifying a test subject that includes: for each of a plurality of training subjects collecting imaging data describing an observed intensity associated with each voxel of a spatial volume of interest; for each of the plurality of training subjects collecting imaging data describing a feature of an observed spatial characteristic associated with each voxel of a spatial volume of interest; constructing a statistical model based on each of the training subjects as a function of the data describing the observed intensity and the feature of the spatial characteristic for each training subject; for each of a plurality of control subjects at least some of which are known to have a condition, collecting imaging data describing an observed intensity associated with each voxel of the intensity volume of interest; for each of the plurality of control subjects, collecting imaging data describing an observed feature of the spatial characteristic associated with each voxel of the spatial volume of interest; for each of the control subjects fitting the imaging data describing an observed intensity associated with each voxel of the intensity volume of interest to the statistical model; for each of the control subjects fitting the imaging data describing an observed feature of the spatial characteristic associated with each voxel of the spatial volume of interest to the statistical model; for the test subject collecting data describing intensity associated with each voxel of the intensity volume of interest; for the test subject collecting data describing the feature of the spatial characteristic associated with each voxel of the spatial volume of interest; classifying the test subject as having or not having the condition, based on a fit of the data describing intensity associated with each voxel of the intensity volume of interest for the test subject and based on a fit of the data describing the feature of the spatial characteristic associated with each voxel of the spatial volume of interest for the test subject, and the fitting of the imaging data for each of the control subjects, to the statistical model.

According to yet another aspect of the invention, there is provided a classification system for classifying a test subject as likely having or not having a condition, the classification system comprising a classifier derived from a statistical model generated from: imaging data for a plurality of training subjects; imaging data for a plurality of control subjects at least some of which are known to have a condition; imaging data for the test subject; an intensity volume of interest (VOI) for intensity analysis and a spatial volume of interest (VOI) for spatial analysis from the imaging data for the training subjects, the control subjects, and the test subject; training intensity data calculated for the intensity VOI for the training subjects and training spatial data calculated for the spatial VOI for the training subjects; and control intensity data calculated for the intensity VOI for the control subjects and control spatial data calculated for the control VOI for the control subjects. The statistical model is based on the training intensity data and the training spatial data to provide a universe of subjects defined in relation to the intensity data and the spatial data. The classifier is derived from the statistical model and utilizes the control intensity data and the control spatial data and divides the universe of intensity and spatial data into a first region of subjects likely having the condition and a second region of subjects likely not having the condition. The classification system is operable to: calculate subject intensity data for the intensity VOI for the test subject and calculate subject spatial data for the spatial VOI for the test subject; and apply the test subject intensity data and the test subject spatial data to the classifier to provide a determination of whether the test subject falls within the first region or the second region.

BRIEF DESCRIPTION OF THE DRAWINGS

In drawings which illustrate by way of example only embodiments of the present invention.

DETAILED DESCRIPTION

Figure 1:
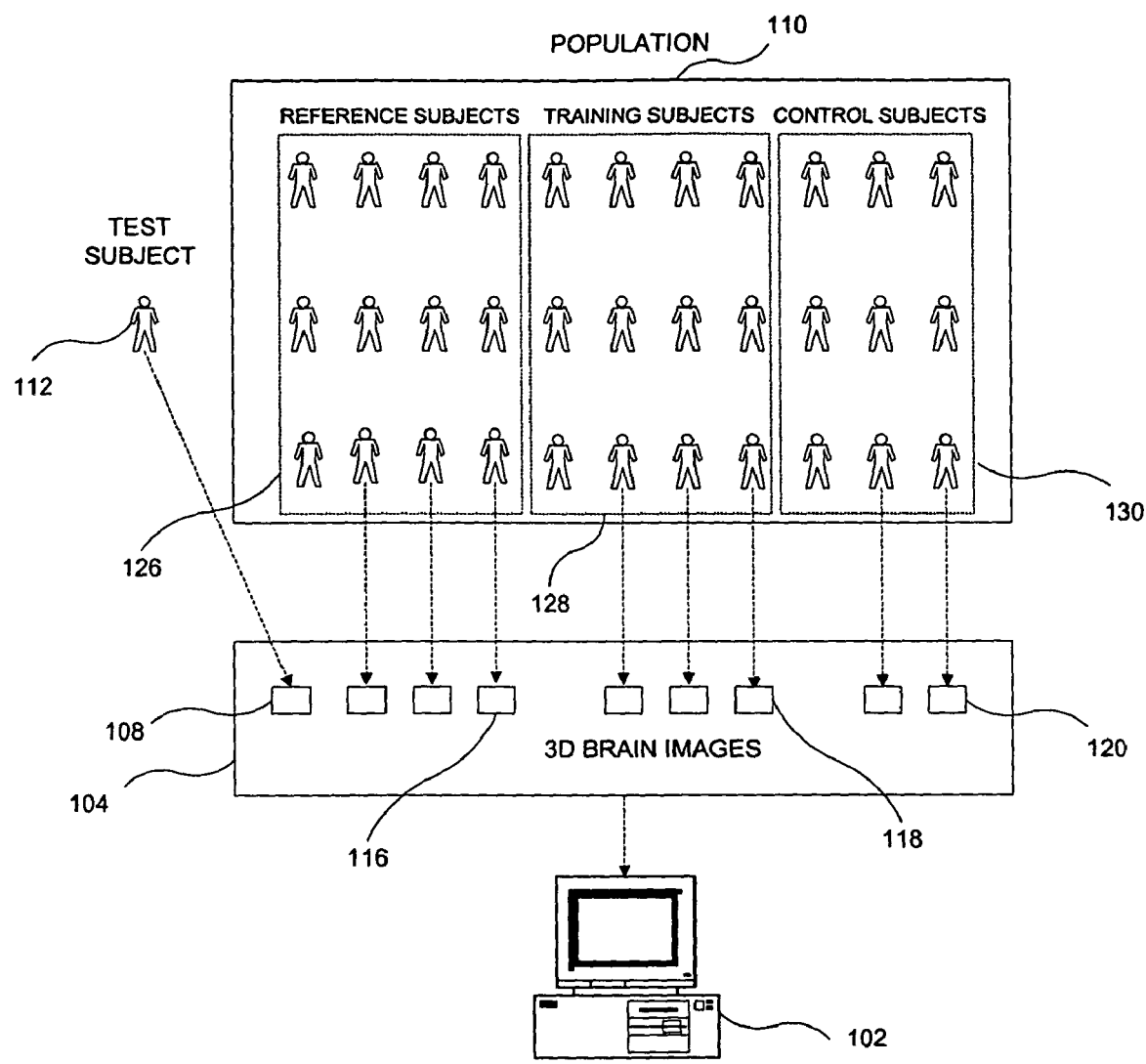
FIG. 1 is a schematic illustration of the design of an automated classification system.

A schematic illustration of the design of an automated classification system 102 in manners exemplary of the present invention is shown in FIG. 1. The example automated classification system 102 determines a classification and diagnosis of the neurological disease state of a given test subject 112, based on 3D image data of the brain 104. The image data 104 may be mono-modal or multi-modal. Possible types of images that may be acquired include, but are not limited to images based on: T1w MRI, T2w MRI, PD MRI, PET, SPECT, and CT.

As illustrated, example automated classification system 102 is determined using a general purpose computing device, executing software exemplary of the aspects of the present invention. The computing device may have any suitable combination of dynamic and persistent storage memory. To classify the disease state of a test subject 112, a plurality of 3D images 104 is first collected from subjects in population 110 (in some embodiments, typically only one image is collected for each subject). The subjects within population 110 consist of three separate groups: reference subjects 126, training subjects 128, and control subjects 130. This results in a set of reference subject images 116, training subject images 118, and control subject images 120. In a preferred embodiment, all subject images are acquired using the same standard, one example for which is described in Mazziotta J C, Toga A W, Evans A, Fox P, Lancaster J, "A probabilistic atlas of the human brain: theory and rationale for its development", The International Consortium for Brain Mapping (ICBM), Neuroimage 1995, 2(2):89-101, the contents of which are incorporated herein by reference.

This image data is presented to the classification system 102 to train itself in the classification of a particular neurological disease or disorder. The automated classification system 102, once trained, may then classify any test subject 112 on the basis of that subject's image data 108.

Figure 2:
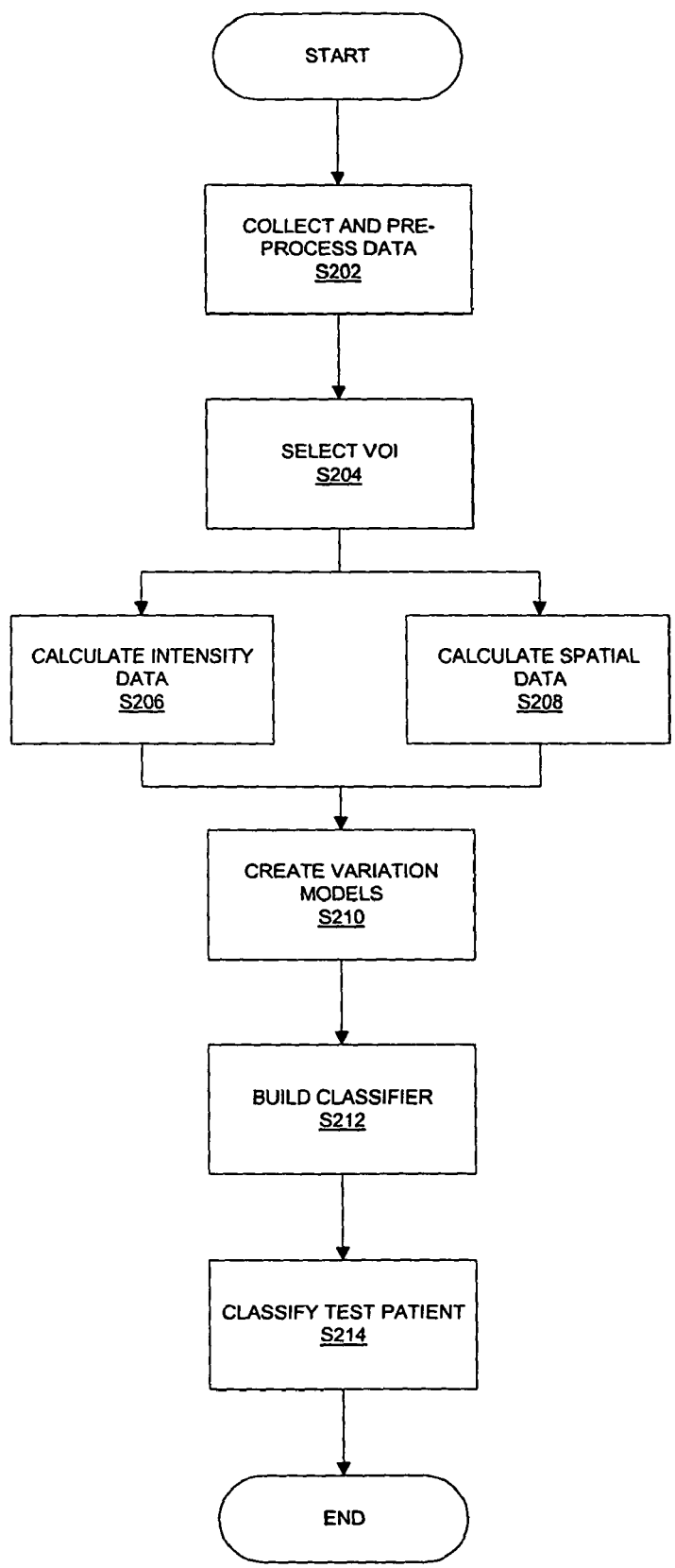
FIG. 2 is a flow chart, illustrating exemplary steps performed at a computing device of FIG. 1

The exemplary steps performed by the automated classification system 102 are illustrated in the flow chart shown in FIG. 2. In step S202, 3D image data 104 is first collected from the scanner and pre-processed. Following image acquisition, known types of preprocessing operations are typically executed to prepare the images for use in analysis in later steps. These preprocessing operations may include the correction of intensity inhomogeneities or global re-alignment (registration) of the image into a standard reference space. Based on standard reference coordinates, one or more particular volumes of interest (VOIs) within the brain are manually selected in step S204, the specific selection of a VOI depending on the particular disease that is to be classified. Both intensity and spatial characteristics of the image data are calculated in steps S206 and S208. These steps define the features of the images that will be analyzed in later steps. Statistical models are created in step S210 based on training subject images 118 and define multi-dimensional spaces within which subjects may be represented. These statistical models are merged to create one single, final multi-dimensional classification space or universe. In step S212, a classifier is built within this classification space based on control group image data 120 and divides the universe of subjects into two or more regions, such that each region defines a space of subjects having a particular condition (or state of nature). This classifier is then used in step S214 to identify and characterize the disease state of individuals, such as a test patient 112, based on the location of an individual's representation within the classification space.

Figure 3:
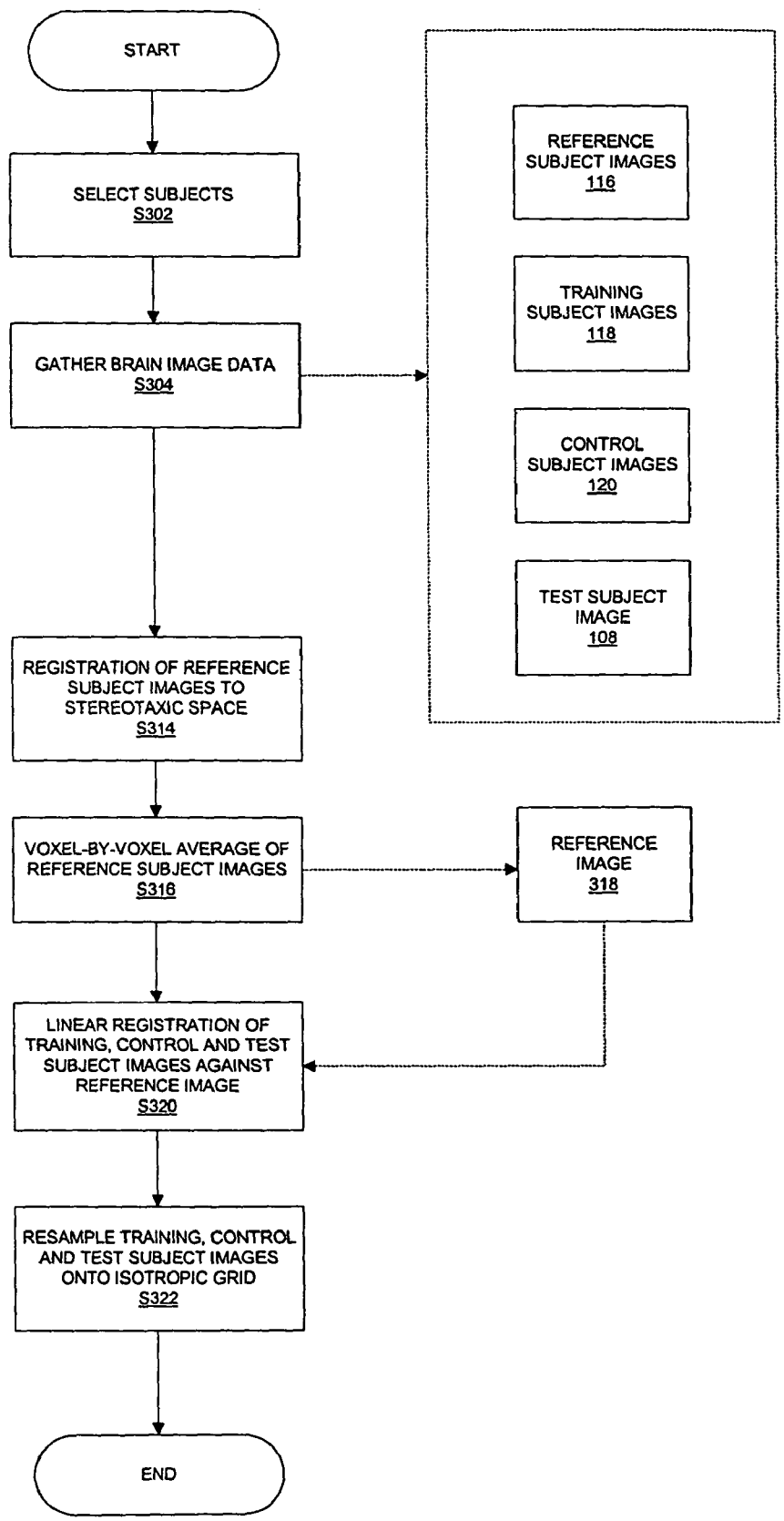
FIG. 3 is a flow chart, further illustrating the data collection step of FIG. 2

The data collection step S202 is more particularly illustrated in FIG. 1 and FIG. 3. Prior to the processing of any data by the automated classification system 102, subjects are selected in step S302. For each selected subject, brain image data is acquired in step S304 using an appropriate medical imaging device. This results in image data 116, 118, 120 for reference subjects, training subjects, and control subjects, respectively. This is the image data that is required in order to build and train the automated classification system 102 to diagnose and classify a particular neurological disease or disorder. Test subject image data 108 is also obtained for the individuals whose neurological disease state is to be diagnosed and classified by the automated classification system 102. Possible types of images that may be acquired include, but are not limited to: T1w MRI, T2w MRI, PD MRI, PET, SPECT, and CT. The nature of the information encoded at each voxel of the image data will depend on the particular imaging modality chosen, and thus the term "intensity" is intended to cover the different possibilities corresponding to the different modalities.

The subjects may be chosen in step S302 in a number of different ways, understood by a person skilled in the art, in order to discriminate between groups of subjects on the hypothesis that there exists intensity and spatial differences between brain images of individuals in the groups. Groups of subjects need not always include "normal" non-pathological individuals. For example, the classifier may be used to separate between groups of pathological individuals. In order to capture the variability between individual subjects within the statistical models, a large enough number of training subjects 128, must be selected. Selecting a minimum of 30-40 training subjects 128 is sufficient. Similarly, the selection of a minimum of 30-40 control subjects 130 is sufficient for determining functions that divide the universe of subjects into classification regions. It is not necessary that the group of control subjects contain known members of each possible condition (or state of nature). For example, pathological individuals of a particular condition (or state of nature) might be classified by the system on the basis of a control group consisting solely of known pathological subjects of that particular condition (in such an embodiment, a different model for the definition of membership within each classification region would be built than one for which the control group contains known member of each possible condition). In a preferred embodiment, the training subject images 118 and the control subject images 120 are obtained from two distinct groups of subjects in order to ensure statistical independence.

Global intensity correction is typically performed on all of the images in order to correct intensity inhomogeneities due to scanner variations (not shown in FIG. 3.) A number of standard techniques may be used to accomplish this. Two such techniques are described in J. G. Sled, A. P. Zijdenbos, and A. C. Evans, "A Nonparametric Method for Automatic Correction of Intensity Nonuniformity in MRI Data", IEEE Transactions on Medical Imaging, Vol. 17, No. 1, February 1998, pp. 87-97, and Van Leemput K, Maes F, Vandermeulen D, Suetens P, "Automated model-based bias field correction of MR images of the brain", IEEE Trans Med Imaging 1999, 18(10):885-96 the contents of which are hereby incorporated by reference.

As illustrated in FIG. 3., after subject selection S302 and brain image acquisition S304 there are different sets of subject images, 116, 118, 120, and 108. Each set of subject images serves a different purpose in the automated classification system 102. The present system does not require that all of these images be pre-processed in step S202 as shown in FIG. 3 at the same time (e.g. the test subject images 108 may be pre-processed at a separate time, possibly at a clinic for diagnosis).

Reference subject images 116 facilitate the comparison of the image data between different individuals by being the basis for the formation of a single reference image 318 against which all other images may be registered. After the reference image 318 is formed, the reference subject images 116 are no longer needed. The linear registration of an image against a reference image 318 in step S320 will globally align the image into a standard reference space, such as the Talairach space (a normalized coordinate system commonly used in the field of neuroscience). For example, the linear registration technique described in D. L. Collins, P. Neelin, T. M. Peters, and A. C. Evans, "Automatic 3D Intersubject Registration of MR Volumetric Data in Standardized Talairach Space", Journal of Computer Assisted Tomography, Vol 18(2), March/April 1994, pp. 192-205, the contents of which are hereby incorporated by reference, describes a method based on a 3D cross-correlation with an average brain image volume. An image may be quantitatively determined to be aligned into a standard reference space through the minimization of an error or cost function based on the cross-correlation of image gradients. Thus, reference subject images 116 are first each registered with a standard reference space in step S314. A voxel-by-voxel average of all of the reference subject images is then taken in step S316 to create a final, single reference image 318.

Training subject images 118 are used to build the statistical model, which are the mathematical variation models which define multi-dimensional spaces within which subjects may be represented. Control subject images 120 are used to build mathematical functions that will identify and characterize the disease state of individuals. Test subject images 108 are used to represent a test patient 112 who is to be classified by the classification system 102. All of these subject images are linearly registered in step S320 against the reference image 318. For example, a 9-degrees of freedom (3 translational, 3 rotational, 3 scaling) linear transformation that maximizes the cross-correlation between characteristics of a subject image and the reference image 318 at each voxel might be employed to accomplish the linear registration in step S320. Other linear transformation techniques can be employed in other embodiments. Initial processing of the subject images also includes resampling the data onto an isotropic grid in step S322. In a preferred embodiment, an isotropic grid with a resolution of 1 mm$^3$ is used. Other known pre-processing techniques that can be employed include AIR and SPM, described in Woods R P, Grafton S T, Watson J D, Sicotte N L, Mazziotta J C, "Automated image registration: II. Intersubject validation of linear and nonlinear models", Journal of Computer Assisted Tomography 1998, 22(1):153-165 and described in Ashburner J, Friston K J, "Voxel-based morphometry—the methods", Neuroimage 2000, 11(6 Pt 1):805-2100, respectively, the contents of each being incorporated herein by reference.

After image data has been collected and pre-processed in step S202 a large, non-specific volume of interest (VOI) is selected in step S204. This will typically be done manually by a person with sufficient experience to decide what is a suitable VOI in the particular circumstances. It is, however, contemplated to widen the search space so that even large (more than ⅓) portions of the brain might be sufficient to perform this task, regardless of anatomical variability. It is also contemplated that a computer with artificial intelligence might be programmed to perform this task.

Figure 4:
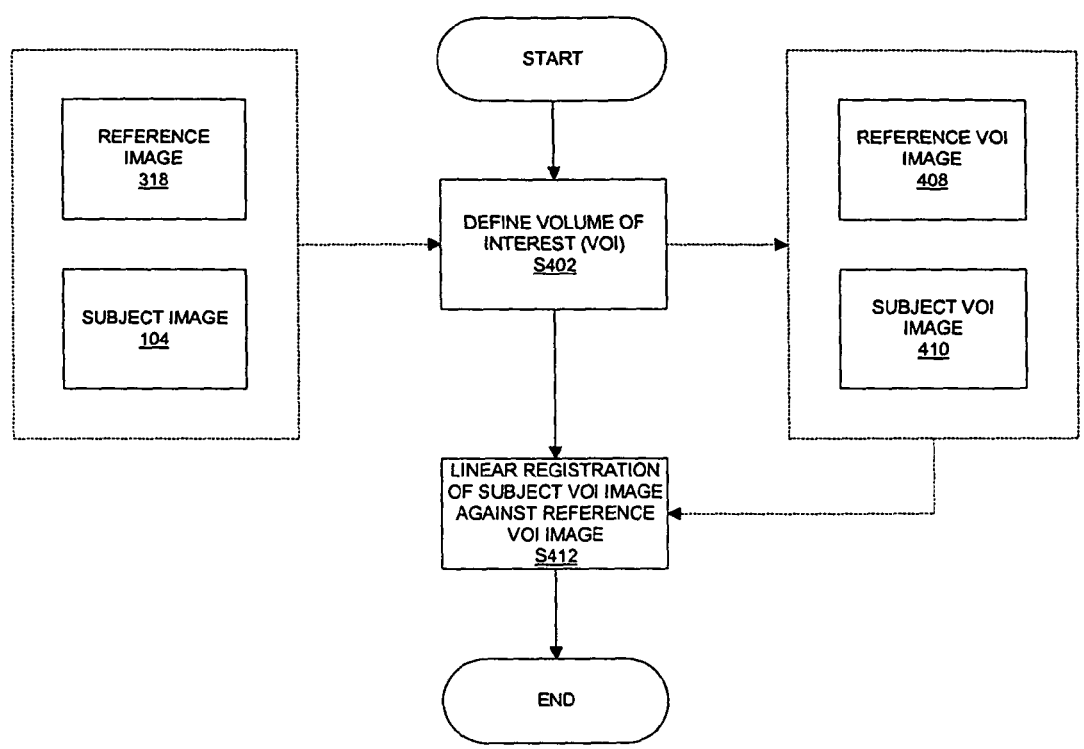
FIG. 4 is a flow chart, further illustrating the VOI selection step of FIG. 2

This step of selecting a VOI is more particularly illustrated in FIG. 4. The present system does not require that this step be performed for all of the subject images 104 at the same time (e.g. the test subject images 108 may be processed at a separate time, possibly at a clinic for diagnosis). The VOI is defined in step S402 for the purpose of extracting a specific portion of a global brain image for analysis. There are a number of advantages to using a relatively large, non-specific VOI. First, the VOI is useful because particular diseases will affect certain areas of the brain more than others. The VOI allows a focused analysis that reduces the noise introduced into the global analyses by parts of the brain outside of the VOI. However, it is not generally the case that only a single anatomical structure of the brain is affected by a given disease. Often there are complex interactions between brain components, which cannot be captured through the analysis of a single brain structure. Thus, the selection of a larger VOI in step S402 that encapsulates more than one brain structure enables the present invention to analyze characteristics of a specific volume in the brain without restricting analysis to a single brain structure.

The VOI will typically be selected to cover a larger region of interest than one specific brain component. Thus the VOI can be selected to encompass one or more specific components of the brain which are known to be associated with a specific pathology, and will provide a boundary that extends a distance beyond the edge of the component(s) of interest.

The VOI is also "non-specific" in the sense that absolute accuracy in the delineation of the boundary of the VOI is not essential. Even if the selection of a given VOI in step S402 is inaccurate (e.g. centimeters off from an optimal selection) the classification system will still likely function properly to classify a test subject. The larger the number of subjects used in training and building the system, the less precise the selection of the VOI needs to be. One practical advantage is that the selection of the VOI in step S402 may possibly be done by an individual who merely has neuro-anatomical knowledge and does not necessarily need to be an individual with special expert medical or neuroscientific knowledge.

The present invention also combines the analysis of different features of both intensity and spatial shape characteristics of images. This allows even greater flexibility in the image analysis, since a different VOI may be selected at step S402 for each particular feature of interest that is to be analyzed. For example, one VOI may be selected for the analysis of a feature based on intensity data, while a second VOI may be selected for the analysis of a feature based on spatial data. The classification system will perform its analysis taking into account both VOIs. Thus, multiple and different VOIs may be defined for any given application of the classification system.

Once a VOI has been defined in step S402, that portion of the image is extracted from the global volume based on its standard reference (e.g. Talairach) coordinates. This extraction is performed for a given subject image 104 as well as the reference image 318, resulting in a reference VOI image 408 and a subject VOI image 410. To further reduce any positional variations in brain structures due to normal inter- and intra-individual variability not eliminated during the linear registration step S320 (since that step is a global registration of the entire image and not just the selected VOI), the subject VOI image 410 is linearly registered against the reference VOI image 408. For example, a 12-degrees of freedom (3 translational, 3 rotational, 3 scaling, 3 skewing) linear transformation that maximizes the cross-correlation between characteristics of a subject VOI 410 and the reference VOI 408 at each voxel might be employed to accomplish the linear registration. Some other possibilities for this linear registration of the subject VOI image against the VOI image include using fewer degrees of freedom, however a 12-degrees of freedom transform substantially reduces the "barrel effect", due to gradient coil inhomogeneity.

Figure 5:
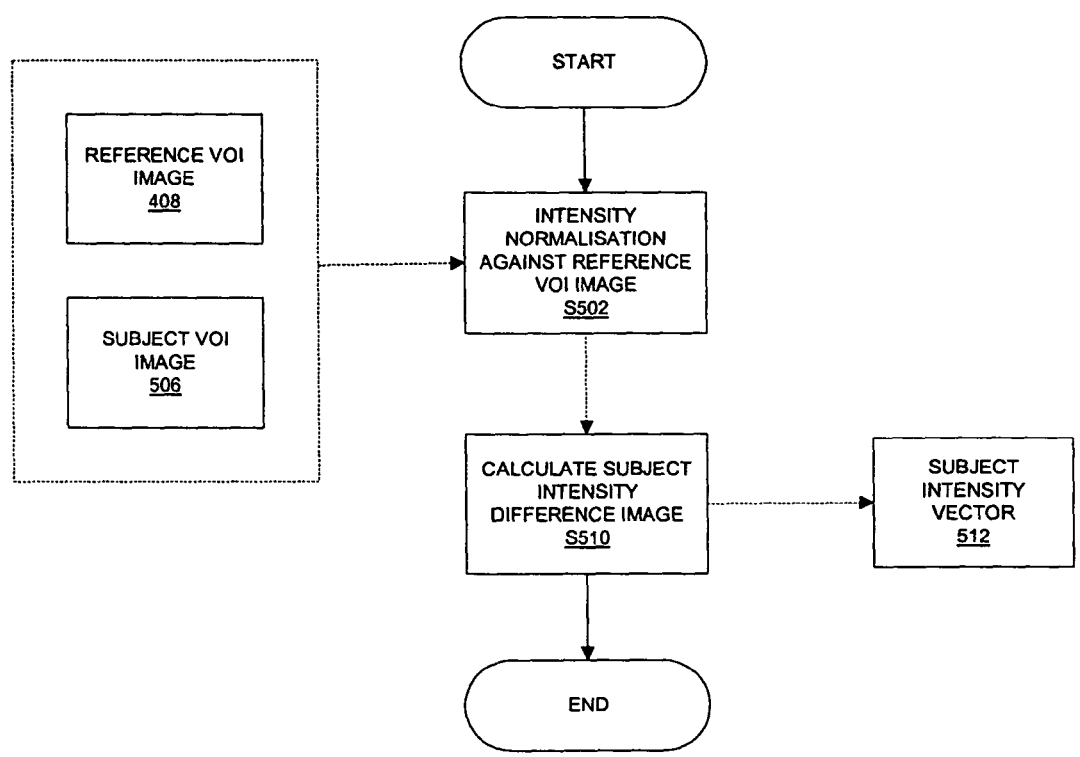
FIG. 5 is a flow chart, further illustrating the intensity data calculation step of FIG. 2

In step S206, training subject images 118, control subject images 120, and test subject images 108, are intensity processed as illustrated in FIG. 5. The present system does not require that all of these images be processed at the same time (e.g. the test subject images 108 may be processed at a separate time, possibly at a clinic for diagnosis). Intensity data for a given subject VOI image 506 is first intensity normalized in step S502 with respect to the reference VOI image 408 to reduce unwanted noise from the analysis. This produces a normalized subject VOI image. In intensity modeling, non-linear registration of the VOI is not performed because it would induce conformity in all data sets, potentially eliminating the pathological effects that are being modeled at the same time as the normal, anatomical variability.

Training subject normalized images 118, control subject normalized images 120, and test subject normalized images 108 are rasterized in step S510 to produce a subject intensity vector (i.e. single vector created by "unwrapping" the 3D image data). Subject intensity vector (g) 512 represents a particular feature of the VOI of a given subject. For example, the feature may be the voxel-by-voxel difference between a subject VOI image 506 and the mean of all subject VOI images 506 in the training group. The resulting subject intensity vector 512 would be:

$$g = v_{subject} - v_{average}$$

Other intensity based features might be determined through the use of texture operators to calculate voxel-wise higher-order intensity features.

Figure 6:
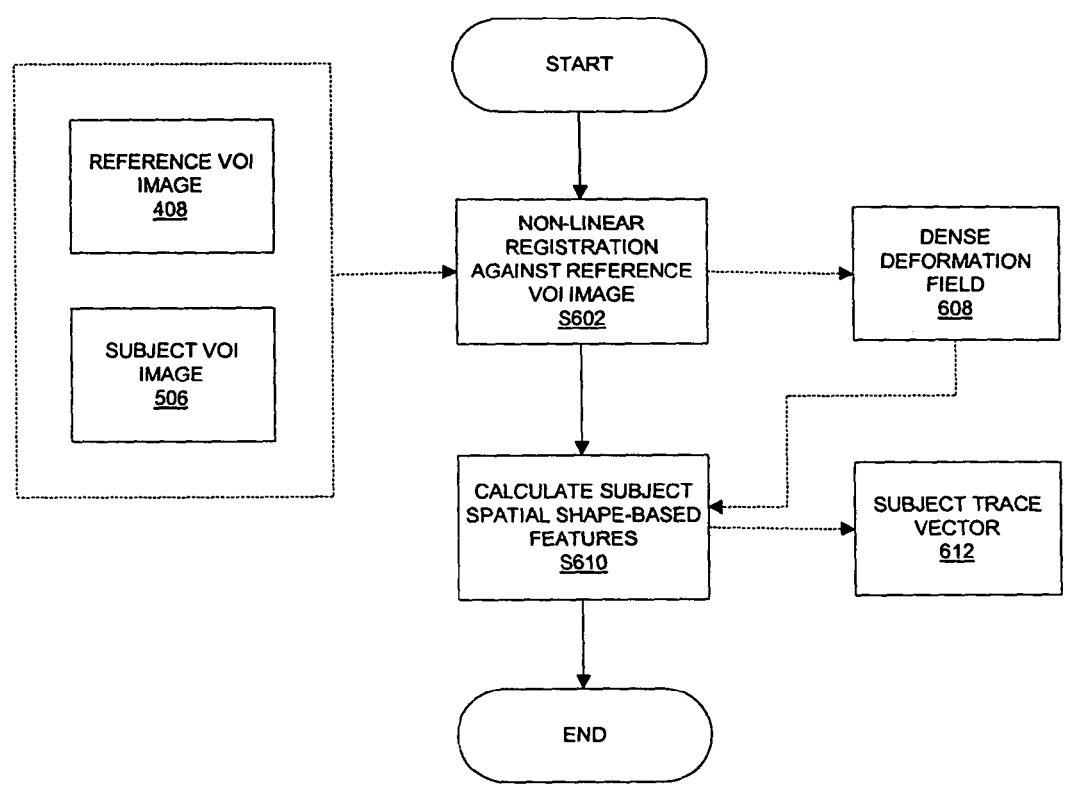
FIG. 6 is a flow chart, further illustrating the spatial data calculation step of FIG. 2

Spatial data is calculated for each subject VOI as well. In step S208, training subject images 118, control subject images 120, and test subject images 108, are processed for spatial shape-based features, as illustrated in FIG. 6. The present system does not require that all of these images be processed at the same time (e.g. the test subject images 108 may be processed at a separate time, possibly at a clinic for diagnosis). A non-linear registration of a given subject VOI image 506 against the reference VOI image 408 is performed first in step S602. Non-linear registration S602 attempts to match image features from a source volume to those of the reference image at a local level. The result of the non-linear registration is a dense deformation field 608 that captures the displacements required to align the subject VOI image 506 to the reference VOI image 408. A number of non-linear registration processes exist for performing this process. One example is ANIMAL, described in D. L. Collins, C. J. Holmes, T. M. Peters, and A. C. Evans, "Automatic 3-D Model-Based Neuroanatomical Segmentation", Human Brain Mapping, Vol. 3, 1995, pp. 190-208, the contents of which are hereby incorporated by reference. The ANIMAL algorithm attempts to match image grey-level intensity features at a local level in successive blurring steps, by minimizing the cross-correlation function of voxel intensities between source and reference images. For example, the non-linear transformation (represented by a deformation field 608) may first be determined at a low resolution (highly blurred data) with 8 mm of spacing between the nodes. The results are refined recursively by increasing the resolution to 4 mm, then 2 mm, and finally 1 mm. Another possible approach to non-linear registration may be to register the VOI using basis functions, and then perform an analysis of the basis function weights.

A series of calculations are performed in step S610 on the resulting dense deformation field 608 to produce a rasterized vector which represents a particular feature of the VOI of a given subject such as local volume change. Other examples might include torque or shift magnitude. A method of computing the local volume change at each voxel by using the rate of the Jacobian change of the deformation is described by M. K. Chung, K. J. Worsely, T. Paus, C. Cherif, D. L. Collins, J. N. Giedd, J. L. Rapoport, and A. C. Evans, "A Unified Statistical Approach to Deformation-Based Morphometry", NeuroImage, Vol. 14(3), 2001, pp. 595-606, the contents of which are hereby incorporated by reference. If U represents the deformation field which matches homologous points between two images by storing a 3-D displacement vector for each voxel, then the deformation in the Lagrangian coordinate system at time t is:

$$x \rightarrow x + U(x,t)$$

The local volume change of the deformation in the neighbourhood of any given voxel at a point x is determined by the Jacobian determinant J which is defined as:

$$J(x,t) = \det\left(I + \frac{\partial U}{\partial x}\right)$$

where I denotes the identity matrix and 3×3 displacement gradient matrix $\nabla U$ is:

$$\nabla U = \frac{\partial U}{\partial x}(x,t) = \begin{pmatrix} \frac{\partial U_1}{\partial x_1} & \frac{\partial U_1}{\partial x_2} & \frac{\partial U_1}{\partial x_3} \\ \frac{\partial U_2}{\partial x_1} & \frac{\partial U_2}{\partial x_2} & \frac{\partial U_2}{\partial x_3} \\ \frac{\partial U_3}{\partial x_1} & \frac{\partial U_3}{\partial x_2} & \frac{\partial U_3}{\partial x_3} \end{pmatrix}$$

For relatively small displacements, the trace of the 3×3 displacement gradient $\nabla U$ is a crude yet indicative measure of local volume change:

$$J \approx 1 + tr(\nabla U)$$

Thus, a rasterized subject trace vector (t) 612, calculated at step S610, is an indicator of morphological change and represents a particular feature of the VOI of a given subject 506 (namely, the local volume change at each voxel). If the feature is the voxel-by-voxel difference between a subject VOI image 506 and the mean of all subject VOI images 506 in the training group, the resulting subject trace vector 612 would be:

$$t = v_{subject} - v_{average}$$

where, $$v = v_{local\ volume\ change} \approx tr(\nabla U)$$

One possible implementation of the trace calculation is discussed in A. L. Janke, G. de Zubicaray, S. E. Rose, M. Griffin, J. B. Chalk, and G. J. Galloway, "4D Deformation Modeling of Cortical Disease Progression in Alzheimer's Dementia", Magnetic Resonance in Medicine, Vol. 46, 2001, pp. 661-666, the contents of which are hereby incorporated by reference.

Another possibility for spatial modeling may be to use each of the differential elements in the displacement gradient matrix $\nabla U$ for tensor-based morphometry as described in Thompson P M, Giedd J N, Woods R P, MacDonald D, Evans A C, Toga A W, "Growth patterns in the developing brain detected by using continuum mechanical tensor maps", Nature 2000, 404(6774):190-3, the contents of which are incorporated herein by reference.

Figure 7:
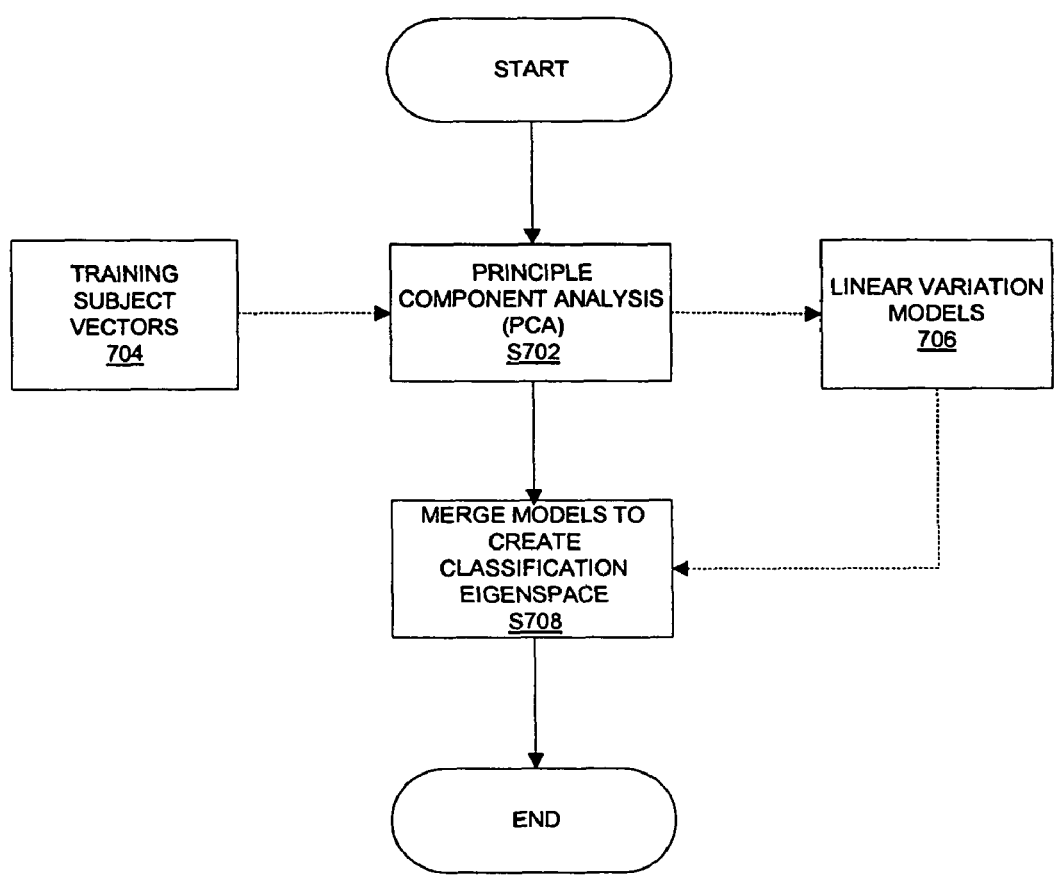
FIG. 7 is a flow chart, further illustrating the variation model creation step of FIG. 2

The creation of variation models in step S210 is more particularly illustrated in FIG. 7. In step S702 training subject vectors 704 are analyzed using Principal Components Analysis (PCA). In the intensity data and spatial data calculation steps S206, S208 discussed previously, a set of vectors are created that represent particular features of the VOI of a given training subject. For example, for each training subject there may exist a training subject trace vector (t) 612 and a training subject intensity vector (g) 512. Linear variation models 706 are created for each particular feature (e.g. one for local volume change and one for intensity difference).

For a given feature, if there are N subjects in the entire set of training subjects, and there are L number of voxels in the VOI, then each subject is a point in L-dimensional space. For example, each training subject trace vector (t) 612 is a vector of length L and the entire model training subject dataset 704 for the trace feature may be expressed in matrix form:

$$\begin{matrix} t_{1,1} & \cdots & t_{1,L} \\ M & & O \\ t_{N,1} & & t_{N,L} \end{matrix}$$

Application of PCA in step S702 to the model training subject dataset 704 results in a set of eigenvectors that characterize the training data. After this stage, the training subject data is no longer needed, as the statistical model has now been generated. As long as N<<L, then the total number of non-zero eigenvectors of the covariance matrix is N−1. These resulting eigenvectors may then be used to create a statistical model of the appearance of the image. For example, a linear variation model 706 can be generated that can describe any instance of a subject trace vector based on the training subject dataset 704. For example, using the notation identical to that in employed in T. F. Cootes, G. J. Edwards, and C. J. Taylor, "Active Appearance Models", IEEE Transactions on Pattern Analysis and Machine Intelligence, Vol. 23, No. 6, June 2001, pp. 681-685 (the contents of which are hereby incorporated by reference):

$$t = t_{mean} + P_t b_t$$

where $t_{mean}$ is the mean normalised trace vector, $P_t$ is the set of orthogonal modes of variation (eigenvectors) for the trace data and $b_t$ is a vector of parameters. A given subject trace vector is described by varying $b_t$. The upper bound on the dimensionality of $P_t$ and $b_t$ is the total number of eigenvectors, which is N−1.

Similarly, a linear variation model 706 may also be generated for the training intensity data:

$$g = g_{mean} + P_g b_g$$

A linear variation model 706 is generated for each set of training subject vectors 704 that represent a particular feature of the VOI. Generalized forms of the model training subject matrix 704 and linear variation model 706 are shown below.

$$\begin{matrix} x_{1,1} & \cdots & x_{1,L} \\ M & & O \\ x_{N,1} & & x_{N,L} \end{matrix}$$

$$x = x_{mean} + P_x b_x$$

where $$x_{mean} = \frac{1}{N} \sum_{i=1}^{N} x_i$$

$P_x$ is the set of orthogonal modes of variation; and
$b_x$ is a vector of parameters The ensemble of principal components from each of the linear variation models 706 define an Allowable Domain as the space of all possible elements expressed by the eigenvectors. For example, an Allowable Grey Domain G is defined by the intensity eigenvectors and an Allowable Trace Domain T is defined by the trace eigenvectors. We now wish to reduce the dimensionality of these Allowable Domains from the upper-bound of N−1. For example, in order to determine how each principle component contributes to the total variance of the system, the ratio of relative importance of the eigenvalue $\lambda_k$ associated with the eigenvector k might be used:

$$r_k = \frac{\lambda_k}{\sum_{j=1}^{N-1} \lambda_j}$$

where the fraction $r_k$ is the relative importance for eigenvalue $\lambda_k$. This information may be employed to reduce the dimensionality of the Allowable Domains by retaining fewer than N−1 eigenvectors, thus defining a restricted space Allowable Grey Doman G* and a restricted Allowable Trace Domain T*. It is contemplated that other types of linear variation models might also be created using other analytical methods, such as independent component analysis.

In step S708, the restricted spaces are merged to create a single, final classification eigenspace or universe C*. It is within this eigenspace that subjects are classified, based on their expressed eigencoordinates. For example, classification eigenspace C* may be created by merging restricted Allowable Trace Domain T* and restricted Allowable Grey Domain G*. Individuals can thus be represented in the space:

$$C^* = T^* \cup G^*$$

Figure 8:
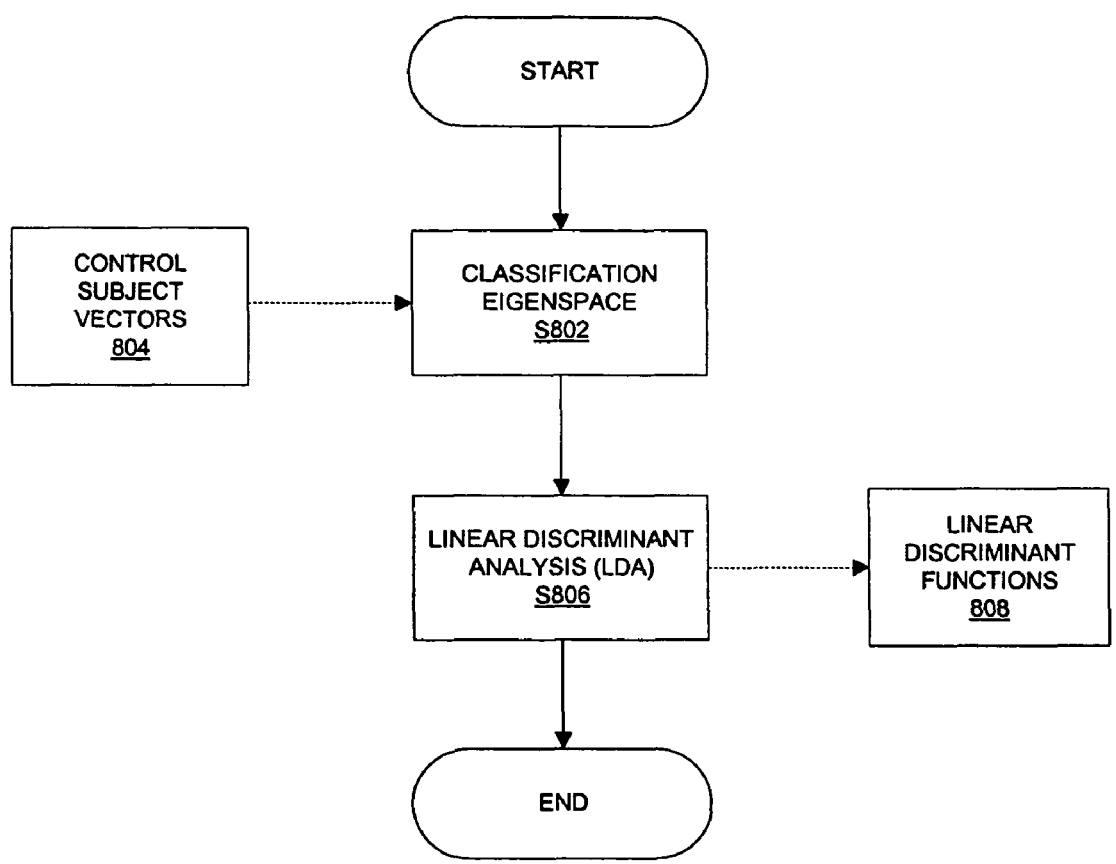
FIG. 8 is a flow chart, further illustrating the classifier building step of FIG. 2

The classifier building step S212 is more particularly illustrated in FIG. 8. In this step, control subject vectors 804 are used to create discriminant functions 808 that divide the eigenspace into regions to classify a given test subject 112 (e.g. one region for those test subjects likely to have a particular disease state and one region for those that are unlikely to have the disease state). The control group dataset thus contains as many homogeneous groups of individuals as necessary for the classification problem. Each individual in the control group is assigned a state of nature $\omega$. For example, two states of nature may be defined in the system: $\omega_1$ for normal subjects and $\omega_2$ for patients. Each control subject vector 804 is projected into the classification eigenspace C*.

In the intensity data and spatial data calculation steps S206, S208 discussed previously, a set of vectors are created that represent particular features of the VOI of a given control subject. The vector representing a particular feature for each control group subject i, belonging to state $\omega$, is projected into the corresponding restricted Allowable Domain for that feature. For example, if each control subject i has a control subject trace vector (t) 612 and a control subject intensity vector (g) 512, then vector (t) 612 of each subject i belonging to state $\omega$ is projected into Domain T* forming eigencoordinate vector $\tau_i$. Similarly, vector (g) 512 is projected into Domain G* forming eigencoordinate vector $\gamma_i$.

A number of possible features may be calculated on the distribution of eigencoordinate vectors. One possibility is to use the eigenposition along the principal component axis. If the distribution of the eigencoordinate vectors is assumed to be normal (Gaussian) then the formulation of feature vectors c for each subject i within classification eigenspace C* may be represented as:

$$c_i^\omega = \gamma_i^\omega \cup \tau_i^\omega$$

where $\omega$ indicates which state the control subject belongs to.

Based on the control group subject data 804, a multivariate linear discriminant analysis (LDA) classifier is built in the classification eigenspace C*, in step S806. Linear discriminant functions 808 are defined for this purpose. For example, if there are two states $\omega_1$ and $\omega_2$, the following discriminant function $f(c)$ 808 might be built:

$$f(c) = w^d c + w_0$$

where w is the weight vector, d represents the dimension of classification eigenspace C*, c is the feature vector of a subject expressed in eigencoordinates, and $w_0$ is the bias or threshold weight. The parameters into a given linear discriminant function 808 (weight vector and bias/threshold weight) determine the orientation and location of a linear decision boundary. These parameters are based on the control group subject data 804. For example, these parameters may be set automatically using statistics software such as SYSTAT, JMP IN or MATLAB.

For a two-state classifier, the classification rule for linear discriminant function 808 may be stated as:

decide $\omega_1$ if $f(c)>0$ and $\omega_2$ if $f(c) \leq 0$

Though not necessary to the present invention, in an effort to further reduce the dimensionality of the classification eigenspace C*, it is possible to select only the most significant eigenvectors for classification in C*, based on the control group subject data 804. This might be done in a multi-level fashion, by selecting the most significant eigenvectors in each Allowable Domain separately (e.g. T* and G*). These spaces would be combined to form a new classification eigenspace of reduced dimensionality. Forward stepwise regression, backward stepwise regression and Wilks' lambda statistics are among the numerous methods that may be used in the determination of significant eigenvectors in this process.

Figure 9:
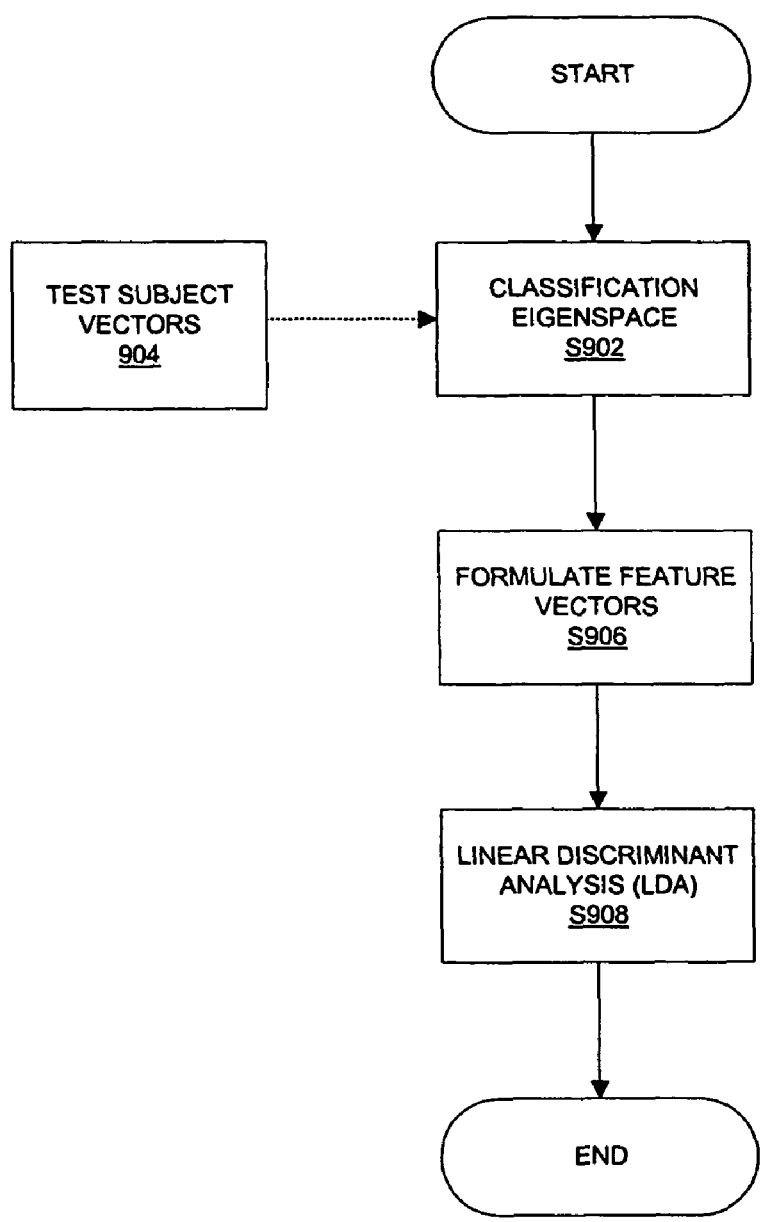
FIG. 9 is a flow chart, further illustrating the test patient classification step of FIG. 2

The classification of a new test patient 112 in step S214 is more particularly illustrated in FIG. 9. In the intensity data and spatial data calculation steps S206, S208 discussed previously, a set of vectors are created that represent particular features of the VOI of a given test subject. The vector representing a particular feature for the test subject 112 is projected into the classification eigenspace C* in step S902 in the same manner as described above for the control group subject data 804 to formulate a feature vector for that subject in step S906. The resulting feature vector is then analyzed according to LDA discriminant functions 808 built in the classification building step S212. Other types of classifiers that might be employed include logistic regression, artificial neural networks and support vector machines.

The automated classification system 102 has been successfully applied to temporal lobe epilepsy (TLE) lateralization, as described in S. Duchesne, N. Bernasconi, A. Bernasconi, D. L. Collins, "Temporal lobe epilepsy lateralization based on MR image intensity and registration features", Conference Proceedings of MICCAI, Springer Verlag, (2003), 2879(1): 367-374, the contents of which are incorporated herein by reference. TLE is defined by seizures originating in the medial temporal lobe (MTL). Since the majority of TLE patients are resistant to anticonvulsant drugs but can be helped by surgery, the present invention is useful in the automated lateralization of the seizure focus as being left or right MTL in origin. Currently, lateralization is performed on the basis of volumetric analysis of hippocampal atrophy and requires a priori segmentation of the hippocampus.

In the data collection step S202, the population subjects 110 are selected. They consist of 150 reference subjects (taken from the International Consortium for Brain Mapping database), 150 training subjects (in this case, the same set of subjects as the reference subjects), and 138 control subjects (consisting of 51 normal subjects and 87 patients). The normal subjects in the control group are different from those in reference and model training group. The patients in the control group are further subdivided into groups of patients with left TLE (47) and right TLE (40) as determined by manual volumetry. 3D MRI brain images are gathered in step S304 for each subject using a 1.5 T scanner T1-fast field echo sequence.

Recent observations in patients with TLE, in N. Bernasconi, A. Bernasconi, Z. Caramanos, S. B. Antel, f. Andermann, and D. L. Arnold, "Mesial temporal damage in temporal lobe epilepsy: a volumetric MRI study of the hippocampus, amygdala and parahippocampal region", Brain, Vol. 126(Pt 2), February 2003, pp. 462-9, the contents of which are hereby incorporated by reference, indicate that the epileptogenic zone is broad. The research suggests that the substrate for seizure generation is distributed over a network of brain structures in the MTL and not just the hippocampus. Thus, in this application, a large non-specific VOI centred on the left MTL is selected in step S204, capturing the hippocampus and neighbouring structures. The VOI is 360800 voxels in size (55×82×80).

This application uses both intensity and trace vectors. The calculation of intensity data in step S206 consists of the voxel-by-voxel difference between a subject VOI image and the mean of all subject VOI images in the training group, resulting in the following subject intensity vector 512:

$$g = v_{subject} - v_{average}$$

The calculation of spatial data in step S208 consists of the trace of the Jacobian matrix of the deformation field for a given subject VOI image, which is an indicator of morphological change (namely, the local volume change at each voxel). This results in the following subject trace vector 612:

$$t = v_{subject} - v_{average}$$

where, $$v = v_{local\ volume\ change} = tr(\nabla U)$$

The creation of linear variation models 706 in step S210 is based on intensity and trace model subject training vectors 512, 612. The first 25 eigenvectors for each model (25 trace, 25 intensity) were chosen, for a total of 50 eigenvectors in the classification space.

Three states of nature are defined for the classifier building step S212. Normal subjects ($\omega_1$), left TLE ($\omega_2$), and right TLE ($\omega_3$). The prior probabilities for each state of nature are $p(\omega_1) = 0.37$, $p(\omega_2) = 0.34$, and $p(\omega_3) = 0.29$. The first classification performed distinguishes between normal ($\omega_1$) and TLE ($\omega_2, \omega_3$) states. A backward stepwise regression is used, which reduces the number of eigenvectors kept from 50 to 20. The second classification performs lateralization of the TLE. A forward stepwise regression with identical tolerance as previously used is employed.

To classify each test patient 112 in step S214, a feature vector is formulated in step S908 for each test subject 112:

$$p_i^\omega = \gamma_i^\omega \cup \tau_i^\omega$$

In this example, the results of classifying each subject in the control group as a test subject 112 are summarized below. Table 1 summarizes the results of the first classification between normal and patient subjects (accuracy 95%) and Table 2 summarizes the results of the TLE lateralization (accuracy 75%).

TABLE 1

True positive results on the Normals—Normals/TLE—TLE diagonal, shown in bold.

|  | Normals | TLE | % correct |
|---|---|---|---|
| Normals | 45 | 6 | 88 |
| TLE | 1 | 86 | 99 |
| Total | 46 | 92 | 95 |

TABLE 2

True positive results on the Left—Left/Right—Right diagonal, shown in bold.

|  | Left | Right | % correct |
|---|---|---|---|
| Left | 36 | 11 | 77 |
| Right | 11 | 29 | 73 |
| Total | 47 | 40 | 75 |

Another example of the successful application of the automated classification system 102 is its application to the successful computerized differentiation of Alzheimer's dementia (AD) and mild cognitive impairment (MCI) from normal aging (NA). AD is a progressive neurodegenerative disorder. Currently, the diagnosis of clinically probable AD can be made with high accuracy in living subjects only once the stage of dementia has been reached, and requires clinical, neuropsychological and imaging assessments. Early detection of AD is therefore critical if treatment is to be effective.

In the data collection step S202, the population subjects 110 are selected. They consist of 152 reference subjects, 152 training subjects, and 44 control subjects (consisting of 22 normal subjects, 15 subjects with AD, and 7 subjects with MCI). 3D MRI brain images are gathered in step S304 for each subject with T1-weighted MRI protocol on a 1.5 T scanner using a fast gradient echo sequence.

Neuropathological studies, such as in J. R. Petrella REC, P. M. Doraiswamy, "Neuroimaging and Early Diagnosis of Alzheimer Disease: A Look to the Future", Radiology 2003, 226(2):315-336, the contents of which are incorporated herein by reference, have shown that brain degeneration occurs very early in the course of the disease, even before the first clinical signs, in certain regions such as the medial temporal lobe (MTL). In this application, a large non-specific VOI centred on the left MTL is selected in step S204. The VOI is 55×82×80=360800 voxels in size and captures the hippocampus and neighboring MTL structures, such as the parahippocampal gyrus.

Both intensity and trace vectors are employed in this application. Intensity data in calculated in step S206 by taking the voxel-by-voxel difference between a subject VOI image and the mean of all subject VOI images in the training group, resulting in the following subject intensity vector 512:

$$g = v_{subject} - v_{average}$$

The calculation of spatial data in step S208 consists of the trace of the Jacobian matrix of the deformation field for a given subject VOI image, which is an indicator of morphological change (namely, the local volume change at each voxel). This results in the following subject trace vector 612:

$$t = v_{subject} - v_{average}$$

where, $$v = v_{local\ volume\ change} \approx tr(\nabla U)$$

Linear variation models 706 are created in step S210 based on intensity and trace model subject training vectors 512, 612. The first 40 eigenvectors were chosen for the classification eigenspace.

Three states of nature are defined for the classifier building step S212, normal subjects ($\omega_1$), AD subjects ($\omega_2$), and MCI subjects ($\omega_3$). The prior probabilities for each state of nature are $p(\omega_1)=0.50$, $P(\omega_2)=0.34$, and $p(\omega_3)=0.16$. Forward stepwise regression was used to select eigenvectors that yielded maximal discrimination between the groups. The first classification distinguishes between normal ($\omega_1$) and AD ($\omega_2$) states, after reducing the number of eigenvectors from 35 to 3 with the stepwise process. The second classification distinguishes between normal ($\omega_1$) and AD+MCI ($\omega_2$, $\omega_3$) states, after reducing the number of eigenvectors from 40 to 2 with the regression model. The third classification distinguishes between AD ($\omega_2$) and MCI ($\omega_3$) states, after reducing the number of eigenvectors from 20 to 3 with the regression model.

Tables 1, 2 and 3 summarizes the results of the three classifications, respectively.

TABLE 1

True positive results on the AD—AD/Normal—Normal diagonal, shown in bold.

|  | AD | Normal | % correct |
|---|---|---|---|
| AD | 15 | 0 | 100 |
| Normal | 0 | 22 | 100 |
| Total | 15 | 22 | 100 |

TABLE 2

True positive results on the AD + MCI-AD + MCI/Normal—Normal diagonal, shown in bold.

|  | AD + MCI | Normal | % correct |
|---|---|---|---|
| AD + MCI | 22 | 0 | 100 |
| Normal | 0 | 22 | 100 |
| Total | 22 | 22 | 100 |

TABLE 3

True positive results on the AD—AD/MCI—MCI diagonal, shown in bold.

|  | AD | MCI | % correct |
|---|---|---|---|
| AD | 12 | 3 | 80 |
| MCI | 0 | 7 | 100 |
| Total | 12 | 10 | 90 |

These examples serve to illustrate the potential applicability of the present automated classification system to the detection of neurological diseases or disorders. Schizophrenia is another example of a neurological disorder that the present invention may be applied to. The system might also be applied as a differentiator between Alzheimer's dementia and other types of dementia such as frontal lobe dementia, Parkinson dementia, and vascular dementia. Studies on movement disorders may also be potentially conducted using the present invention.

The aforementioned and other features, benefits and advantages of the present invention can be understood from this description and the drawings by those skilled in the art. The above described exemplary embodiments of this invention are intended to be illustrative and in no way limiting. Many modifications are possible in the exemplary embodiments without materially departing from the novel teachings and advantages of this invention. All such modifications are intended to be encompassed within the scope of the present invention, as defined by the claims.

The invention claimed is:

1. A method of classifying a test subject comprising:

for each of a plurality of training subjects collecting imaging data describing an observed image attribute associated with each voxel of a first volume of interest;

for each of said plurality of training subjects collecting imaging data describing a feature of an observed image morphometry attribute associated with a second volume of interest;

constructing a statistical model based on each of said training subjects as a function of both said imaging data describing an observed image attribute associated with each voxel of said first volume of interest and said imaging data describing a feature of said observed image morphometry attribute associated with said second volume of interest for said each training subject;

for each of a plurality of control subjects at least some of which are known to have a condition, collecting imaging data describing an observed image attribute associated with each voxel of said first volume of interest; for each of said plurality of control subjects, collecting imaging data describing a feature of said observed image morphometry attribute associated with said second volume of interest;

for each of said control subjects fitting said imaging data describing an observed image attribute associated with each voxel of said first volume of interest to said statistical model, wherein said statistical model is built to contain data characterizing subjects involving a linear registration of voxels in said first volume of interest;

for each of said control subjects fitting said imaging data describing a feature of said observed image morphometry attribute associated with said second volume of interest to said statistical model, wherein said statistical model is built to contain data characterizing subjects involving a non-linear registration of voxels in said second volume of interest;

for said test subject collecting imaging data describing an observed image attribute associated with each voxel of said first volume of interest;

for said test subject, collecting imaging data describing a feature of said observed image morphometry attribute associated with said second volume of interest;

classifying, in a computer, said test subject as having or not having said condition, based on a fit, involving a linear registration of voxels in said first volume of interest, of said imaging data describing an observed image attribute associated with each voxel of said first volume of interest for said test subject and based on a fit, involving a non-linear registration of voxels in said second volume of interest, of said imaging data describing a feature of said observed image morphometry attribute associated with said second volume of interest for said test subject, and said fitting of said imaging data for each of said control subjects, to said statistical model.

2. A method as claimed in claim 1 wherein said second volume of interest is substantially the same as said first volume of interest.

3. A method as claimed in claim 1 wherein said second volume of interest is not the same as said first volume of interest.

4. A method of classifying a test subject from imaging data of body tissue, comprising:
   processing in a computer imaging data from said test subject and imaging data from a reference patient or model, without explicit segmentation of structures of interest, to perform a linear registration between said first VOI of said test subject imaging data and said reference patient or model imaging data and to obtain at least one first value representing a spatial voxel attribute feature within said first VOI of said test subject imaging data referenced with respect to said reference patient or model imaging data;
   processing in a computer said test subject imaging data and said reference patient or model imaging data, without explicit segmentation of structures of interest, to perform a non-linear registration between said second VOI of said test subject imaging data and said reference patient or model imaging data and to obtain at least one second value representing a spatial voxel morphological relationship between said second VOI of said test subject imaging data to said second VOI of said reference imaging data; and
   classifying in a computer said test subject using both said first value and said second value with respect to similar said first and second values from known classification imaging data.

5. The method as defined in claim 4, further comprising:
   selecting a first volume of interest (VOI) and a second volume of interest (VOI) wherein said first VOI and said second VOI are not specific to a specific structure of said body tissue relevant to classification purposes.

6. The method as defined in claim 5, wherein said first VOI and said second VOI comprise a plurality of structures of said body tissue relevant to classification.

7. The method as defined in claim 6, wherein said classifying is related to a disease state.

8. The method as defined in claim 4, wherein said body tissue is brain tissue.

9. The method as defined in claim 8, wherein said classifying is related to a disease state.

10. The method as defined in claim 9, wherein said first VOI and said second VOI are selected to encompass one or more specific structures of the brain which are known to be associated with a specific pathology, and will provide a boundary that extends a distance beyond the edge of the structures of interest.

11. The method as defined in claim 9, wherein said disease state includes Alzheimer's disease.

12. The method as defined in claim 9, wherein said disease state includes epilepsy.

13. The method as defined in claim 4, wherein said classifying is related to a disease state.

14. The method as defined in claim 4, wherein a classification dataset is first built using said reference subject imaging data without using said test subject imaging data, and then said classifying comprises analysis of said at least one first value and said at least one second value with respect to said classification dataset.

15. The method as defined in claim 14, wherein said classification dataset represents a single classification eigenspace, said at least one first value and said at least one second value being merged as they are projected in said eigenspace.

16. The method as defined in claim 15, wherein said at least one first value and said at least one second value are ensembles of vector-value voxels.

17. The method as defined in claim 16, wherein said rasterized vectors represents a difference between voxel intensity of said test subject imaging data, as linearly registered, and an average voxel intensity of said reference patient imaging data within said first VOI, and the trace of the Jacobian of a deformation field for a given subject VOI.

18. The method as defined in claim 17, wherein principal components analysis is used to create said eigenspace.

19. The method as defined in claim 15, wherein principal components analysis is used to create said eigenspace.

20. The method as defined in claim 4, wherein said at least one first value and said at least one second value are rasterized vectors.

21. The method as defined in claim 20, wherein said rasterized vectors represents a difference between voxel intensity of said test subject imaging data, as linearly registered, and an average voxel intensity of said reference patient imaging data within said first VOI, and the trace of the Jacobian of a deformation field for a given subject VOI.

22. The method as defined in claim 4, wherein said first VOI is the same as said second VOI.

23. A classification apparatus for processing subject imaging data and classification in accordance with a classification model, the apparatus comprising:
   a test subject imaging data processor for performing both linear and non-linear registrations between at least one volume of interest of said test subject imaging data and reference imaging data to obtain data characterizing said test subject imaging data both as a function of intensity and of morphology, wherein said at least one volume of interest is much larger than a specific feature relevant to classification purposes;
   a classifier for classifying said test subject using said data characterizing said test subject imaging data and said model, wherein said classifying uses both intensity and morphology of image attributes with said at least one volume of interest.

* * * * *